(12) United States Patent
Pomytkin

(10) Patent No.: US 8,673,977 B2
(45) Date of Patent: Mar. 18, 2014

(54) CHOLINE SALTS OF SUCCINIC ACID FOR THE TREATMENT OF DEPRESSION, ANXIETY, SCHIZOPHRENIA, SLEEP DISORDER, AND EPILEPSY

(75) Inventor: Igor Anatolievich Pomytkin, Moscow (RU)

(73) Assignee: Igor Anatolievich Pomytkin, Moscow (RU)

( * ) Notice: Subject to any disclaimer, the term of this patent is extended or adjusted under 35 U.S.C. 154(b) by 265 days.

(21) Appl. No.: 13/129,739

(22) PCT Filed: Nov. 26, 2008

(86) PCT No.: PCT/RU2008/000720
§ 371 (c)(1),
(2), (4) Date: May 17, 2011

(87) PCT Pub. No.: WO2010/062206
PCT Pub. Date: Jun. 3, 2010

(65) Prior Publication Data
US 2011/0237668 A1    Sep. 29, 2011

(51) Int. Cl.
*A61K 31/195*    (2006.01)
*A01N 37/44*    (2006.01)

(52) U.S. Cl.
USPC .......................................... 514/561; 514/557

(58) Field of Classification Search
None
See application file for complete search history.

(56) References Cited

U.S. PATENT DOCUMENTS

2010/0144773 A1 * 6/2010 Pomytkin ................... 514/276

FOREIGN PATENT DOCUMENTS

| RU | 2281765 | 8/2006 |
|----|---------|--------|
| RU | 2281766 | 8/2006 |
| RU | 2228174 | 5/2010 |
| WO | WO 2009096807 A1 * | 8/2009 |
| WO | WO 2010033045 A1 * | 3/2010 |

OTHER PUBLICATIONS

Litt et al., Awareness without recall during anesthesia for electroconvulsive therapy, Anesthesiology, (Apr. 2007) vol. 106, No. 4, pp. 871-872.*
Okamoto et al., Efficacy of electroconvulsive therapy is associated with changing blood levels of homovanillic acid and brain-derived neurotrophic factor (BDNF) in refractory depressed patients: a pilot study, Progress in Neuro-Psychopharmacology and Biological Psychiatry, (Jul. 1, 2008) vol. 32, No. 5, pp. 1185-1190.*
Cupello et al., Catatonic features in major depression relieved by electroconvulsive treatment: Parallel evaluation of the status of platelet serotonin transporter. International Journal of Neuroscience, (Oct. 2008) vol. 118, No. 10, pp. 1460-1466.*
Mayrhofer (Mayrhofer OK, Self-experiments with succinylcholine chloride; a new ultra-short-acting muscle relaxant. Br Med J. 1952, 1(4772), p. 1332, first column, last block).
Davenport et al. (Davenport HT, McDonald AW. Succinylcholine, a Short-acting Relaxant. Can Med Assoc J. 1953, 68(2), p. 140, first column, last block).
Griffith (Griffith HR. Succinycholine—a controllable muscle relaxant. Can Med Assoc J. 1954, 71(1), p. 29, first column, last block).

* cited by examiner

*Primary Examiner* — Svetlana M. Ivanova
(74) *Attorney, Agent, or Firm* — Notaro, Michalos & Zaccaria P.C.

(57) ABSTRACT

The present invention relates to compositions and methods for treatment of depression, anxiety, schizophrenia, sleep disorder, or epilepsy comprising monocholine salt of succinic acid of a formula (I) or a pharmaceutically acceptable salt thereof. Preferably, the pharmaceutically acceptable salt is dicholine salt of succinic acid of a formula (II).

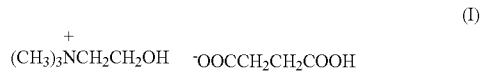

(I)

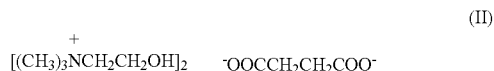

(II)

6 Claims, No Drawings

CHOLINE SALTS OF SUCCINIC ACID FOR THE TREATMENT OF DEPRESSION, ANXIETY, SCHIZOPHRENIA, SLEEP DISORDER, AND EPILEPSY

FIELD OF THE INVENTION

The present invention relates to pharmaceutical compositions and methods for the prevention or treatment of depression, anxiety, schizophrenia, sleep disorder, and epilepsy. More particularly, the present invention relates to the use of monocholine succinate salts in pharmaceutical compositions and methods for the treatment depression, anxiety, schizophrenia, sleep disorder, and epilepsy.

BACKGROUND OF THE INVENTION

RF patent 2228174 discloses the use of dicholine salt of succinic acid for the treatment of insulin resistance, diabetes, hyperlipidemia, and dyslipidemia. RF patent 2281765 discloses the use of dicholine salt of succinic acid for the treatment of cerebral ischemia. RF patent 2281766 discloses the use of dicholine salt of succinic acid for the improvement of cognitive function.

However, nothing is published or disclosed in the art related to the use of choline salts of succinic acid for treating depression, anxiety, schizophrenia, sleep disorder, and epilepsy.

Surprisingly, it has been found that monocholine and dicholine salts of succinic acid are useful for treating depression, anxiety, schizophrenia, sleep disorder, and epilepsy.

It is an object of the present invention to provide compositions and methods for treating depression, anxiety, schizophrenia, sleep disorder, and epilepsy with the use of choline salts of succinic acid.

DETAILED DESCRIPTION OF THE INVENTION

The present invention provides a method of treating depression, anxiety, schizophrenia, sleep disorder, or epilepsy comprising administering to a mammal in need thereof an effective amount of monocholine salt of succinic acid of a formula (I)

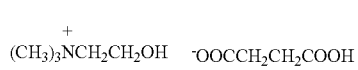

(I)

or a pharmaceutically acceptable salt thereof.

As used herein, the term "depression" refers to a mental disorder typically characterized by a lasting sad mood and/or lost of interest or pleasure in most activities. Examples of depression disorders which may preferred be treated using an effective amount of a named compound or pharmaceutically acceptable salt thereof include, but are not limited to: major depressive disorder also known as major depression, unipolar disorder, or clinical depression; major depressive episode; atypical depression; depression (mood); melancholic depression; psychotic depression; and postpartum depression.

As used herein, the term "anxiety" refers to an anxiety disorder. Examples of anxiety disorders which may preferred be treated using an effective amount of a named compound or pharmaceutically acceptable salt thereof include, but are not limited to: panic attack; agoraphobia; acute stress disorder; specific phobia; panic disorder; psychoactive substance anxiety disorder; organic anxiety disorder; obsessive-compulsive anxiety disorder; posttraumatic stress disorder; generalized anxiety disorder; and anxiety disorder NOS.

As used herein, the term "schizophrenia" refers to a psychiatric disorder that includes at least two of the following: delusions, hallucinations, disorganized speech, grossly disorganized or catatonic behavior, or negative symptoms. Patients can be diagnosed as schizophrenic using the DSM-IV criteria (APA, 1994, Diagnostic and Statistical Manual of Mental Disorders (Fourth Edition), Washington, D.C.), and the World Health Organization's International Statistical Classification of Diseases and Related Health Problems, the ICD-10.

As used herein, the term "sleep disorder" refers to a disruptive pattern of sleep arising from many causes. Examples of sleep disorders which may preferred be treated using an effective amount of a named compound or pharmaceutically acceptable salt thereof include, but are not limited to: insomnia (e.g., transient, short-term, and chronic), delayed sleep phase syndrome, hypnotic-dependent sleep disorder, and stimulant-dependent sleep disorder; disorders associated with difficulties in staying awake such as sleep apnea, narcolepsy, restless leg syndrome, obstructive sleep apnea, central sleep apnea, idiopathic hypersomnia, respiratory muscle weakness-associated sleep disorder; disorders associated with difficulties in adhering to a regular sleep schedule such as sleep state misperception, shift work sleep disorder, chronic time zone change syndrome, and irregular sleep-wake syndrome; disorders associated with abnormal behaviors such as sleep terror disorder (i.e., parasomnia) and sleep-walking (i.e., somnambulism); and other disorders such as sleep bruxism, fibromyalgia, and nightmares.

As used herein, the term "epilepsy" refers to a disorder of brain function characterized by recurrent unprovoked seizures.

As used herein, the term "treating" refers to the management and care of a mammal for the purpose of (a) preventing the disorder from occurring in a subject which may be predisposed to such disorder but has not yet been diagnosed as having it; (b) inhibiting the disorder, i.e., arresting its development; or (c) relieving the disorder, i.e., causing regression of the disorder.

As used herein, the term "succinic acid", which is also named butanedioic acid, refers to a compound of formula $HOOCCH_2CH_2COOH$, CAS RN 110-15-6.

As used herein, the term "a pharmaceutically acceptable salt" refers to non-toxic base addition salts. The pharmaceutically acceptable salts of the present invention are prepared by a reaction of succinic acid with a pharmaceutically acceptable organic or inorganic base by methods well-known from the art. Such bases include, but are not limited to, nontoxic alkali metal and akaline earth bases, for example, calcium, lithium, sodium, and potassium hydroxide; ammonium hydroxide and nontoxic organic bases, such as triethylamine, butylamine, dimethylethanolamine, diethanolamine, triethanolamine, and 2-ethyl-6-methyl-3-hydroxypyridine, and choline base.

In a preferred embodiment of the present invention, the pharmaceutically acceptable salt of the present invention is dicholine salt of succinic acid of a formula (II)

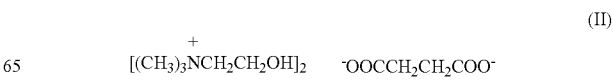

(II)

As used herein, the term "an effective amount" refers to the amount of the succinic acid or a pharmaceutically acceptable salt thereof that is required for treating depression, anxiety, schizophrenia, sleep disorder, or epilepsy in a subject in need thereof. Effective amounts may vary, as recognized by those skilled in the art, depending on route of administration, excipient usage, and the possibility of co-usage with other agents.

Preferably, the effective amount of the monocholine salt of succinic acid of a formula (I) or a pharmaceutically acceptable salt thereof for the use in the method of the present invention is 0.1 to 100 mg/kg body weight per day. More preferably, the effective amount of the monocholine salt of succinic acid of a formula (I) or a pharmaceutically acceptable salt thereof for use in the method of the present invention is 1 to 10 mg/kg body weight per day.

The monocholine salt of succinic acid of a formula (I) or a pharmaceutically acceptable salt thereof may be administered to a mammal by a variety of routes. Preferably, the monocholine salt of succinic acid of a formula (I) or a pharmaceutically acceptable salt thereof is administered by a route selected from the group consisting of oral, oromucosal, sublingual, buccal, intranasal, topical, parenteral, intraocular, intramuscular, subcutaneous, intravenous, and intraperitoneal administration in a variety of dosage forms. Such dosage forms include, but are not limited to, tablets, capsules, powders, solutions, water solutions, aerosols, elixirs, syrups, and injections.

Preferably, the monocholine salt of succinic acid of a formula (I) or a pharmaceutically acceptable salt thereof is administered for a period of one day or longer. More preferably, the monocholine salt of succinic acid of a formula (I) or a pharmaceutically acceptable salt thereof is administered by courses for a period of 5 to 7 days, singly-a-day, with break between courses of two to four weeks.

Preferably, the mammal is a human.

Further, the present invention provides the use of monocholine salt of succinic acid of a formula (I)

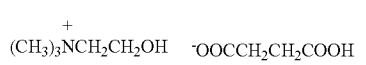
(I)

or a pharmaceutically acceptable salt thereof for manufacturing a pharmaceutical composition for preventing or treating depression, anxiety, schizophrenia, sleep disorder, or epilepsy in a mammal in need thereof.

Further, the present invention provides a pharmaceutical composition for preventing or treating depression, anxiety, schizophrenia, sleep disorder, or epilepsy comprising (a) monocholine salt of succinic acid of a formula (I)

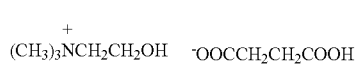
(I)

or a pharmaceutically acceptable salt thereof and (b) a pharmaceutically acceptable carrier.

Preferably, the pharmaceutically acceptable salt is dicholine salt of succinic acid of a formula (II)

(II)

As used herein, the term « pharmaceutically acceptable carrier" refers to a pharmaceutically-acceptable material, composition or vehicle, such as a liquid or solid filler, diluent, excipient, solvent, or encapsulating material, involved in carrying or transporting a chemical agent from one organ or portion of the body to another organ, or portion of the body. Some examples which can serve as pharmaceutically acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The compositions of the invention are prepared by known procedures using well-known ingredients. The composition of the invention can comprise optional ingredients. Such optional ingredients generally are used individually at levels from about 0.0005% to about 10.0%, preferably from about 0.005% to about 1.0% by weight of the composition. Examples of suitable optional ingredients include, but are not limited to, buffers, lubricants, colorants, carriers, and etc.

The compositions of the invention may be administered by a variety of routes. Such routes include, but are not limited to, oral, oromucosal, sublingual, buccal, intranasal, topical, parenteral, intraocular, intramuscular, subcutaneous, intravenous, and intraperitoneal routes of administration.

The following examples are presented to demonstrate the invention. The examples are illustrative only and are not intended to limit the scope of the invention in any way.

Example 1

This example demonstrates preparation of compounds of formula (I) and (II).

A compound of formula (I) is prepared by mixing 12.1 g choline base with 11.8 g succinic acid at room temperature without of a solvent. Resulting mixture is dissolved in acetone at ambient temperature; and the solution is filtered through a filter. Compound (I) is recovered as ionic liquid by evaporating of acetone from the solution. $^1$H NMR in $D_2O$: 2.41 (9H, s), 3.19 (4H, s), 3.49 (2H, t), 4.10 (2H, t). Formula: C9H19NO5.

A compound of formula (II) is prepared by mixing of 2.2 g of the compound of formula (I) with 1.1 g of choline base at ambient temperature without of a solvent. The mixture is dried under vacuum and re-crystallized from isopropanol-acetone. Compound (II) is recovered as a white powder. $^1$H NMR in $D_2O$: 2.35 (18H, s), 3.15 (4H, s), 3.46 (4H, t), 4.00 (4H, t).

Example 2

This example demonstrates that compounds of the present invention are effective for the treatment of depression.

Effect of the treatment of depression with compounds of the invention was assessed in rodents in (A) a forced swim test and (B) a chronic stress depression model.

(A) In the forced swim test, young male CD1 mice, singly housed, were used. Mice were treated i.p. with saline (control) or 25 mg/kg compounds (I) or (II) for 7 days once-a-day and tested at 8$^{th}$ day. In the reference group, mice were treated i.p. with 10 mg/kg Imipramine 30 min prior the swimming test. Forced swim test was done in a glass cylinder 17 cm diameter, water height 13 cm (7 cm to the edge of a cylinder) filled with water at ambient temperature. Animals were scored during 6 min. The latency of the first floating episode was accepted as a measure of forced swim behavior. Statistical analysis was done using ANOVA and Mann-Whitney test as a post-hoc analysis. Data are presented in Table 1 as mean±SEM latency of the first floating episode.

TABLE 1

| Group | Latency, s |
|---|---|
| Control (n = 9) | 24 ± 10 |
| Imipramine (n = 7) | 60 ± 26* |
| Compound (I) (n = 5) | 117 ± 18* |
| Compound (II) (n = 5) | 140 ± 11* |

*Differs significantly of Control (P < 0.05).

(B) In the chronic stress depression model, young male CD1 mice, singly housed, were used. Mice were treated i.p. with saline (control) or 25 mg/kg compound (II) for 7 days once-a-day prior the onset of stress. Stress procedure was used for 10 days. In the reference group, mice received Imipramine orally 8 mg/kg per day for 7 days prior the stress and then in a course on entire 10-days-stress-procedure. Animals (n=20 per group) were tested on a sucrose preference at 10$^{th}$ day of the stress procedure. Statistical analysis was done using ANOVA and Mann-Whitney test as a post-hoc analysis. Data are presented in Table 2 as mean±SEM of a percentage of sucrose preference.

TABLE 2

| Group | Sucrose preference, % |
|---|---|
| Control, non-stressed | 79 ± 4* |
| Control, stressed | 64 ± 4 |
| Imipramine | 75 ± 4* |
| Compound (II) | 72 ± 3* |

*Differs significantly of stressed Control (P < 0.05).

Thus, compounds of the present invention are useful for the treatment of depression.

Example 3

This example demonstrates that compounds of the present invention are effective for the treatment of anxiety.

Effect of the treatment of anxiety with compounds of the invention was assessed in rodents in light/dark transition test. Stressed mice from the Example 2 were tested in a dark/light box as described by Crawley et al., Pharmacol Biochem Behav 13, 167-70 (1980). Animals were scored during 5 min for (i) total time spent in light box and (ii) number of exits. Statistical analysis was done using ANOVA and Mann-Whitney test as a post-hoc analysis. Data are presented in Table 3 as mean±SEM of (i) total time spent in light box and (ii) number of exits.

TABLE 3

| Group | Time, s | Number of exits |
|---|---|---|
| Control, non-stressed | 233 ± 13 | 8.2 ± 0.7 |
| Control, stressed | 208 ± 16 | 8.8 ± 1.1 |
| Compound (II) | 250 ± 11* | 4.8 ± 0.6* |

*Differs significantly of Controls (P < 0.05).

Thus, compounds of the present invention are useful for the treatment of anxiety.

Example 4

This example demonstrates that compounds of the present invention are effective for the treatment of a sleep disorder.

Effect of the treatment of sleep disorder (insomnia) with compound II of the present invention was assessed in caffeine-induced model of insomnia. Rats were treated for 7 days once-a-day with i.p. 25 mg/kg compound II or saline (control). At day 8, 10 mg/kg caffeine significantly prolongs sleep onset latency (SOL) as compared to vehicle in control rats. In rats pretreated with compound II, caffeine did not prolonged SOL as compared to vehicle. Thus, compounds of the present invention are useful for the treatment of the sleep disorder.

Example 5

This example demonstrates that compounds of the present invention are effective for the treatment of schizophrenia.

Effect of the treatment of schizophrenia with compounds of the invention was assessed in rats raised in social isolation (ISO). Isolation rearing of rats is a non-lesion manipulation that leads to deficits in PPI (prepulse inhibition) of the startle reflex and other behavioral and neurochemical alterations similar to that observed in schizophrenics. Weiss I C and Feldon 3, Psychopharmacology, 2001, 156: 305-326. Harte M K, et al., Schizophr. Res. 2006, 81:210-211. Swerdlow N R et al., Arch Gen Psych. December, 2006, 63:1325-1335. Rats were treated for 7 days once-a-day with i.p. 25 mg/kg compound II or saline (control). Rats were socially isolated and prepulse inhibition of startle reaction was measured at 80 dB prepulse and 110 dB pulse intensity with prepulse latency of 100 milliseconds. PPI ratio was calculated as decrease (%) in reaction amplitude to stimuli delivered with prepulse relative to those without prepulse. Statistical analysis was done using ANOVA and Mann-Whitney test as a post-hoc analysis. Data are presented in Table 4 as mean±SEM of prepulse inhibition in %.

TABLE 4

| Group | Prepulse inhibition, % |
|---|---|
| Control (no isolation) | 56 ± 13 |
| Control (social isolation) | 12 ± 14 |
| Compound (II) | 51 ± 9* |

*Differs significantly of Control (social isolation) (P < 0.05).

Thus, compounds of the present invention are useful for the treatment of schizophrenia in animal model.

Example 6

This example demonstrates that compounds of the present invention are effective for the treatment of epilepsy.

Effect of the treatment of epilepsy with compounds of the invention was assessed in mice with seizures induced by pentylenetetrazol. Loscher et al., Epilepsy Res 1991, 8:171-189. Mice were treated for 7 days once-a-day with i.p. 10 mg/kg compound II or saline (control). Pentylenetetrazol was administered. The treatment with compound II significantly decreases seizures as compared to control.

Example 7

This example demonstrates injection formulation comprising compound of formula (I).

| Ingredient | Content |
| --- | --- |
| Compound of formula (I) | 200 mg |
| Disodium phosphate USP/Ph Eur | qs to pH 5.5 |
| Water for injections USP/Ph Eur | to 5.0 ml |

Compound of formula (I) is dissolved in water for injection to the desired volume, 0.4M disodium phosphate is added to pH 5.0. In this manner, solution with concentration of compound of formula (I) of 5% is prepared. The solution is filtered through a sterilizing grade filter (0.2 μm), and filled into ampoules.

Example 8

This example demonstrates injection formulation comprising compound of formula (II).

| Ingredient | Content |
| --- | --- |
| Compound of formula (II) | 200 mg |
| Disodium phosphate USP/Ph Eur | qs to pH 5.5 |
| Water for injections USP/Ph Eur | to 5.0 ml |

Compound of formula (II) is dissolved in water for injection to the desired volume, 0.4M disodium phosphate is added to pH 5.0. In this manner, solution with concentration of compound of formula (II) of 5% is prepared. The solution is filtered through a sterilizing grade filter (0.2 μm), and filled into ampoules.

What is claimed is:

1. A method of treating depression, anxiety, schizophrenia, sleep disorder, or epilepsy comprising administering to a mammal in need thereof an effective amount of monocholine salt of succinic acid of formula (I)

(I)

2. The method of claim 1, wherein the pharmaceutically acceptable salt is dicholine salt of succinic acid of formula (II)

(II)

3. The method of claim 1, wherein the effective amount of monocholine salt of succinic acid of formula (I) or a pharmaceutically acceptable salt thereof is 0.1 to 100 mg/kg body weight per day.

4. The method of claim 1, wherein the monocholine salt of succinic acid of formula (I) or a pharmaceutically acceptable salt thereof is administered by a route selected from the group consisting of oral, oromucosal, sublingual, buccal, intranasal, topical, parenteral, intraocular, intramuscular, subcutaneous, intravenous, and intraperitoneal administration.

5. The method of claim 1, wherein the monocholine salt of succinic acid of formula (I) or a pharmaceutically acceptable salt thereof is administered for a period of one day or longer.

6. The method of claim 1, wherein the mammal is a human.

* * * * *